United States Patent [19]

Roeck et al.

[11] Patent Number: 5,394,455
[45] Date of Patent: Feb. 28, 1995

[54] DIGITALLY AIDED MICROFLUOROSCOPY AND FLUOROSPOT SYSTEM AND METHOD OF USING THE SAME

[75] Inventors: Werner W. Roeck, Irvine; Orhan Nalcioglu, Laguna Beach; John T. Martin, Riverside, all of Calif.

[73] Assignee: The Regents of the University of California, Oakland, Calif.

[21] Appl. No.: 56,266

[22] Filed: Apr. 30, 1993

[51] Int. Cl.6 .............................................. H05G 1/64
[52] U.S. Cl. .................................. 378/98.3; 378/98.2; 378/151
[58] Field of Search ...................... 378/99, 43, 62, 95, 378/150, 151, 152, 153, 98.2, 98.3, 98.7, 98.8; 358/111

[56] References Cited

U.S. PATENT DOCUMENTS 5,117,446  5/1992  Haaker et al. ........................ 378/99

Primary Examiner—David P. Porta
Attorney, Agent, or Firm—Daniel L. Dawes

[57] ABSTRACT

An improvement is made in a high resolution clinical fluoroscopic system by utilizing a beam splitter for selectively directing a fluoroscopic image of an X-ray pattern transmitted through a patient to either a low resolution or high resolution television channel. The low resolution channel operates a low magnification level to provide a macroscopic view of an object of interest in order to orient the patient and object of interest within the center of view. Thereafter, the beam splitter is activated to redirect the fluoroscopic image to a zoom lens which magnifies the image. The magnified image is then scanned by a sensitive CCD-type camera to alternatively produce through the video processor a magnified view of the object of interest at variable magnification having submillimeter resolution. Collimation of the X-ray beam is coordinated with the degree of magnification through the zoom lens to provide for contrast resolution without any substantial increase of the X-ray exposure levels.

15 Claims, 9 Drawing Sheets

DIGITALLY AIDED MICROFLUOROSCOPY AND FLUOROSPOT SYSTEM AND METHOD OF USING THE SAME

BACKGROUND OF THE INVENTION

1. Field of the Invention

The invention relates to the field of in vivo clinical high resolution microfluoroscopy and methodology, and in particular to fluoroscopic imaging systems and methods.

2. Description of the Prior Art

The emphasis in nonevasive radiology is shifted from diagnosis to therapy and is part of a general trend in medicine to less evasive techniques. Rapid progress in imaging technology has eliminated the need for many angiographic procedures, while the development of new materials, miniaturized catheters and instruments have resulted in substitution of nonevasive radiological procedures for the treatment of problems, which were once treated by conventional surgical methods.

This transition in medical practice has also placed new demands on radiographic imaging, especially real-time fluoroscopy. What was one simply an observational method for diagnostic radiology has now become a precision guidance or observational instrument for therapeutic procedures.

However, current microscopic image intensifying-television systems exhibit inadequate submillimeter spatial resolution for the increased demands placed upon real-time fluoroscopic observation. This lack of resolution has become an obstacle to practicing radiologists when attempting to image fine anatomic structures on a real-time basis, even when a high resolution, 1,023 line video system, is used in combination with image intensifier operating in its highest magnification mode. This obstacle, coupled with the increasing use of small guidewires and catheters in peripheral arterial systems, has created a clinical need to effectively image in the submillimeter range during real-time fluoroscopic observation. Present fluoroscopy systems lack the ability to provide the needed magnification with simultaneous contrast resolution at acceptable X-ray exposure rates.

The field of digital fluoroscopy and fluorography has experienced rapid development due to the availability of suitable electronic hardware such as fast analog-to-digital converters that handle high digitization rates required for real-time imaging at video frame rates. Recent improvements in video-based imaging technology, such as those provided by digital frame integration to reduce noise has opened new possibilities for clinical application of microfluoroscopy. While the use of optical magnification through a zoom has been considered for application of medical imaging since at least 1972, see Robbins CD, et al., "*High Performance Continuous Zoom X-Ray Image Intensifier,* "SPI Proc. 1972; 35: 23–32, and even more recently as shown by Rossi et al., "*A Variable Aperture Fluoroscopic Unit for Reduced Patient Exposure,* "Radiology 129:799–802 (1978), and Rudin et al., *Improving Fluoroscopic Image Quality with Continuously vadable zoom magnification,*" Med. Fys. 18(5): 972–977 (1991), resolutions have been unsatisfactory and the diminished field of view has resulted and loss of orientation. In other words, the realization of clinical application of optical zoom concepts in radiology have failed to be realized because orientation of the magnified image with respect to the larger structures within the regions of interest is easily lost when proceeding to the magnified stages. For example, small voluntary or involuntary movements by the patients, while under examination, results in movement of the object of interest completely from the field of view at the high magnification levels. Reorientation of the object of interest within the field of view cannot then be performed at the magnified level. The fluoroscopic image must be unzoomed until the macroscopic view is reobtained, the patient reoriented in the field of view, and then rezoomed to the higher magnification. Further, when enlarged or zoomed images are displayed, higher X-ray patient exposure rates are required in order to obtain acceptable signal-to-noise ratios.

Therefore, what is needed is an improvement which can be made to radiographic imaging systems, which is capable of magnifying images and providing visibility of object detail at 150 microns or less at the monitor with table top exposure levels of not more than 5 Roentgens per minute.

BRIEF SUMMARY OF THE INVENTION

The invention is an improvement in a system for X-ray fluoroscopic video imaging having an image intensifier for generating a dynamic radiographic image of an X-ray pattern and a monitor system for displaying the dynamic radiographic image. The improvement comprises a magnifying lens for magnifying the dynamic radiographic image of the image intensifier, and a high resolution video channel including a highly sensitive camera optically coupled to the magnifying lens for generating a video signal to be sent to the monitor system. The monitor system displays an image of the X-ray pattern provided by the high resolution video channel. As a result, magnified images of the X-ray pattern are provided in video signal format with submillimeter resolution.

The camera in the high resolution video channel is a CCD-type camera. The magnifying lens is a selectively or continuously variable zoom lens.

The improvement further comprises a low resolution video channel for generating a video signal to be sent to the monitor system. The monitor system displays an image of the X-ray pattern provided by the low resolution video channel. An optical beam splitter is optically coupled to the image intensifier and has one optical output coupled to the magnifying lens and a second optical output optically coupled to the camera in the low resolution video channel. The optical beam splitter selectively transmits the dynamic radiographic image from the image intensifier either to the magnifying lens or to the camera in the low resolution video channel upon user command.

The fluoroscopic imaging system includes an X-ray source and an X-ray collimator coupled to the X-ray source. The X-ray collimator has variable collimation. The improvement further comprises a mechanism for selectively varying collimation of X-rays produced by the X-ray source by the X-ray collimator in coordination with the degree of magnification provided by the magnifying lens.

The invention can also be characterized as a digitally aided fluoroscopic system comprising an X-ray source, a variable X-ray collimator coupled to the X-ray source, and a scanning table for positioning a patient above the X-ray source and collimator in a selected position subject to operator control. An image intensifier receives an X-ray pattern from the patient and generates a dynamic radiographic image thereof. An optical beam splitter is optically coupled to the image intensifier for selectively directing the dynamic radiographic image in a selected fashion into one of two available television channels. A conventional television camera with 525 line resolution is optically coupled to the beam splitter for receiving the dynamic radiographic image along the first direction. A digital video processor is coupled to the television camera for processing video information received from the television camera to selectively produce a digitally processed display of the dynamic radiographic image. A variable zoom lens is optically coupled to the optical beam splitter for receiving and variably magnifying the dynamic radiographic image from the image intensifier when the dynamic radiographic image is transmitted by the optical beam splitter along the second direction. A camera in the high resolution television channel generates a video signal and is coupled to the variable zoom lens. The high resolution television channel is coupled to the digital video processor. The digital video processor processes video information received from the high resolution television channel and simultaneously displays a second processed video image from the low resolution television channel, which second image was stored in the memory in the video processor. The variable collimator is selectively controlled to collimate the X-rays from the X-ray source in coordination with the degree of magnification provided by the variable zoom lens. As a result, submillimeter real-time resolution of the X-ray pattern can be obtained. The radiographic image is displayed on the monitor system in a format large enough to provide an enlarged dynamic, real-time presentation to a user while allowing said user to operate within a sterile field.

The system further comprises a laser printer for producing a permanent record of the displays generated by and stored within the video processor.

In the preferred embodiment the image intensifier produces the dynamic light image at a predetermined wavelength, and the variable zoom lens is arranged and configured for maximal transmission at the wavelength.

The invention can also be defined as a method for performing submillimeter, high resolution digital fluoroscopy on a real-time basis. The method comprises the steps of positioning a patient within a digital fluoroscopic X-ray system to bring an object of interest within the patient into a predetermined field of view defined as the region of interest by observing fluoroscopic images of the object of interest through a camera in the low resolution video channel and a real-time television display system. Fluoroscopic examination of the region of interest is redirected to a sensitive camera in the high resolution channel and focused on the region of interest through the fluoroscopic system by means of a variable zoom lens. A video image produced by the sensitive camera in the high resolution video channel is displayed on a real time basis. The magnification of the zoom lens is simultaneously adjusted until a desired degree of magnification is achieved. As a result, orientation of the object of interest is established through the camera in the low resolution channel and immediately switched for detailed examination through the zoom lens and high resolution television channel.

The step of redirecting comprises the step of actuating a beam splitter to direct a dynamic radiographic image of an X-ray pattern of the object of interest selectively to the low or high resolution channels as determined by operator control.

The method further comprising the step of collimating an X-ray beam to which the patient is exposed to develop the fluoroscopic image of the object of interest in coordination with the step of simultaneously controlling magnification of the zoom lens. The step of collimating the beam increases collimation of the X-ray beam as magnification of the dynamic radiographic image increases through control of the variable zoom lens.

The method further comprises the step of generating a dynamic radiographic image of the X-ray pattern within a narrow optical bandwidth. The zoom lens and camera in the high resolution video channel are optimized to operate within the narrow bandwidth of the light spectrum emitted by the image intensifier to increase the optical sensitivity.

The method comprises the steps of repeating the step of positioning the patient when patient movement causes loss of orientation of the object of interest. The patient is selectively positioned by performing the step of redirecting the dynamic radiographic image of the X-ray pattern to the camera in the low resolution channel to reorient the object of interest within the region of interest within the patient. Thereafter the step of redirecting the dynamic radiographic image to the high resolution television channel is repeated once reorientation of the object of interest within the region of interest is established.

The invention may be better visualized by now turning to the following drawings wherein like elements are referenced by like numerals.

The invention in its various embodiments may now be understood by now turning to the following detailed description.

DETAILED DESCRIPTION OF THE PREFERRED EMBODIMENTS

An improvement is made in a clinical fluoroscopic system by utilizing a beam splitter for selectively directing a fluoroscopic image of an X-ray pattern received from a patient to either a low resolution or high resolution channel. The low resolution channel operates at low magnification level to provide a macroscopic view of an object of interest in order to orient the patient and object of interest within the center of view. Thereafter, the beam splitter is activated to redirect the fluoroscopic image to a zoom lens which magnifies the image. The magnified image is then scanned by a highly sensitive CCD-type camera in the high resolution channel to alternately produce through the video processor a magnified view of the object of interest at variable magnification having submillimeter resolution. Collimation of the X-ray beam is coordinated with the degree of magnification through the zoom lens to provide for high spatial resolution without any substantial increase of the X-ray exposure levels.

The improvement of the invention includes modification of existing angiographic X-ray machine by optically coupling a charge coupled device (CCD) television camera via a zoom lens to a beam splitter, while retaining the generic camera system as a parallel channel. The dual system thus affords a fast and easy means of switching between the two camera subsystems by means of an electromechanically operated mirror inside the beam splitter.

Figure 1:
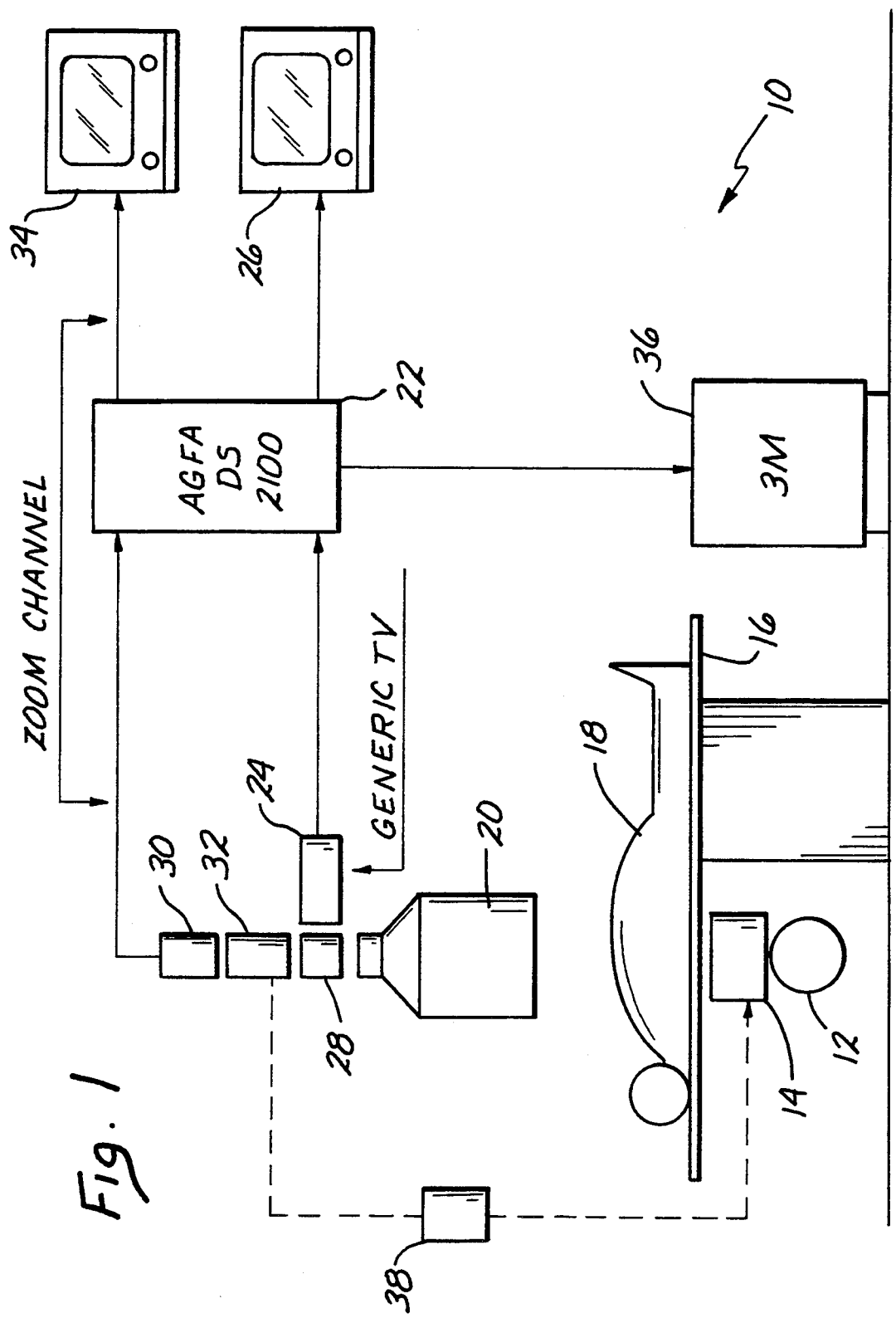
FIG. 1 is a diagrammatic block diagram showing a fluoroscopy system incorporating the improvement of the present invention.

Turn to the diagrammatic depiction of FIG. 1 which shows an illustrative embodiment of the invention. The improved fluoroscopic system, generally denoted by reference numeral 10, is comprised of a biased microfocused X-ray tube 12 preferably with focal spot sizes of 0.13 millimeters and 0.6 millimeters and with 7 and 45 kilowatt rating. A conventional Philips XD6026 collimator system 14 was modified to provide precision coning of collimation during zoom operation as described below.

X-ray tube 12 and collimator 14 are positioned beneath an examination table 16 upon which a patient 18 lies. The transmission X-ray image is received by a 9-inch Thompson HX image intensifier 20 which has been carefully adjusted by refocusing after installation. A spatial resolution in access of 5.0 c/mm is quoted by the manufacturer for the center resolution in the 4.5-inch mode. The luminance homogeneity of the image intensifier in the 4.5-inch mode is better than 8 percent. Brightness gain (Gx) is measured by the manufacturer to be 52 for the 4.5-inch field. The high brightness gain and high spatial resolution characteristics of image intensifier 20 was selected to provide a device suitable for detailed vascular applications.

A conventional 525-line (RS-170) Philips XTV-4 television system was used as the conventional monitoring system and included a Philips Vidicon XQ 1240 pickup tube provided for the input to the conventional television system, which had its output displayed on monitor 26. A AGFA Digistore recording system 22, having a last-frame-hold function and to provide dual displays of the image while performing live fluoroscopy on a second monitor, was employed. The system allowed for noise reduction by integration of 2, 4, 8, or 16 frames during real-time fluoroscopy.

Beam splitter 28 selectively directs the dynamic radiographic image from image intensifier 20 in one of two selected directions as controlled by the attending physician. A second camera 30, a Philips MOD 56471 charge coupled device-type camera (CCD) 30 was coupled with a zoom lens 32, which in turn was directed to the second port of beam splitter 28. CCD-type camera 30 was selected for its light sensitivity characteristics, 0.05 lux minimum sensor illumination, and matched spectral sensitivity to the green light emitted by the output phosphor on image intensifier 20. In the illustrated embodiment, zoom lens 32 was a Canon V6X 18 (DC) CCTV zoom lens mounted on the straight port of beam splitter 28.

Camera 30 in the illustrated embodiment uses a CCD frame transfer image sensor, type NXA 1031-01, with 610 horizontal pixels by 480 vertical pixels when operating in the 30-frame per second mode. Active pixel dimensions are 0.9 microns horizontally and 18.6 microns vertically due to the integration of two pixel lines during the readout process. Because of the nonidentical horizontal and vertical dimensions of the active pixel in the illustrated embodiment, separate vertical and horizontal resolutions were exhibited although it is entirely within the contemplation of the invention that other types of video cameras may be used in which the horizontal and vertical resolutions are identical.

Camera 30 in turn comprises the high resolution channel and is coupled an AGFA DS 2100, and has the resultant image displayed on monitor 34. The image output of the AGFA DS 2100 can be selectively routed to a laser printer 36 to provide a permanent, archival record.

The zoom, focusing, and f-stop control of zoom lens 32 are motorized to facilitate operation by the attending physician. A feedback loop circuit, diagrammatically illustrated by line 38, couples the operation of zoom lens 32 with collimator 14 to provide zoom-dependent X-ray collimation.

It must expressly be understood that the various components described are cited only as an illustration and that any functionally equivalent or generically similar type of instrument now known or later devised could be substituted for any or all the components without departing from the scope of the invention.

Figure 3A:
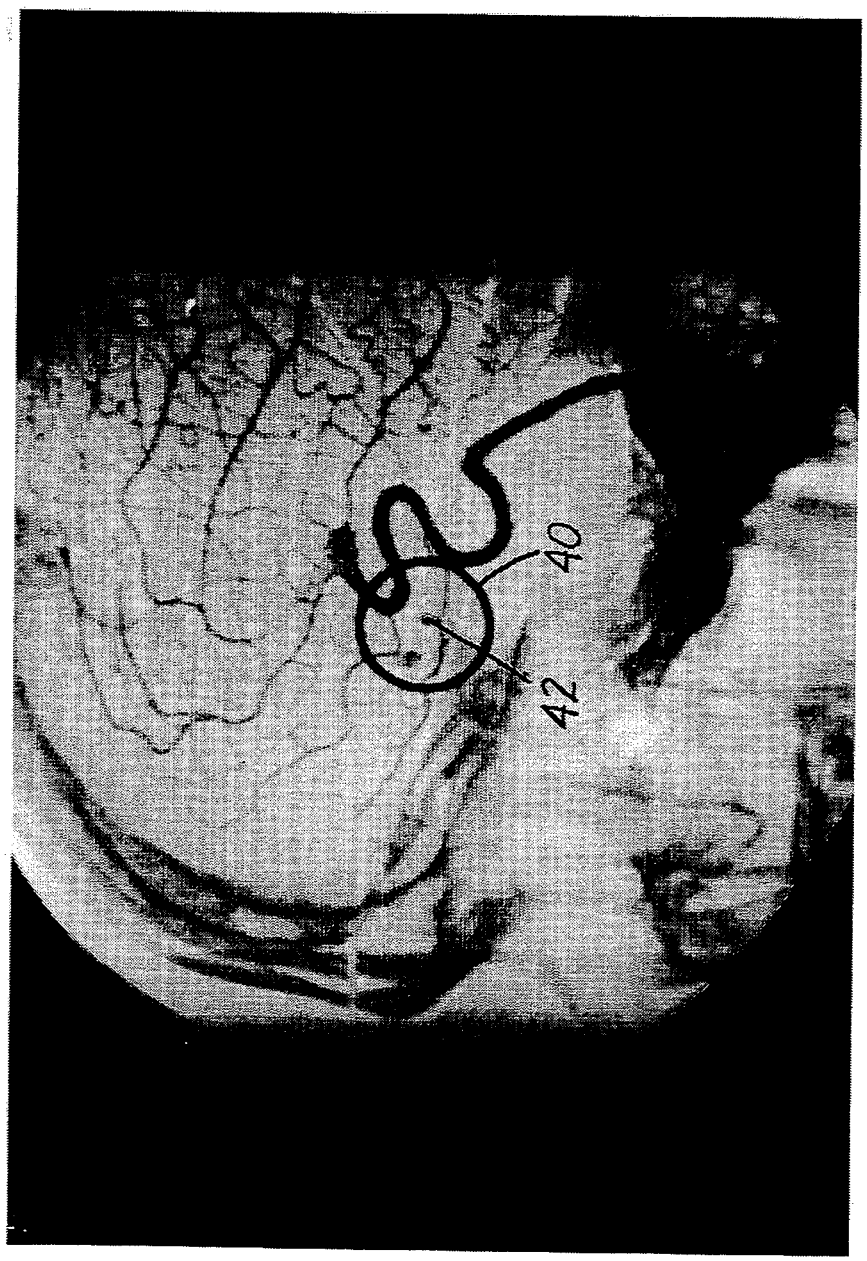
FIGS. 3a and b are fluoroscopic images of a brain aneurysm in a phantom shown in a macroscopic and magnified view respectively as provided by a fluoroscopic system improved according to the invention.

The various components of the system now having been described, consider their operation. The attending physician or system operator positions patient 18 on table 16 to bring the region of interest within patient 18 within the field of view of a 1-inch center ring such as shown in the depiction of FIG. 3a which is a phantom simulation of a brain aneurysm 42. The full field reference image of FIG. 3a is recorded by camera 24 and captured by video processor 22 for fixed display on monitor 26. Thereafter, the operator may adjust the zoom level under live fluoroscopic observation utilizing camera 30 and zoom lens 32. Any desired field size is selectable through the continuous zoom adjustability of lens 32 to fit the optimal display magnification as determined by the attending physician.

Figure 3B:
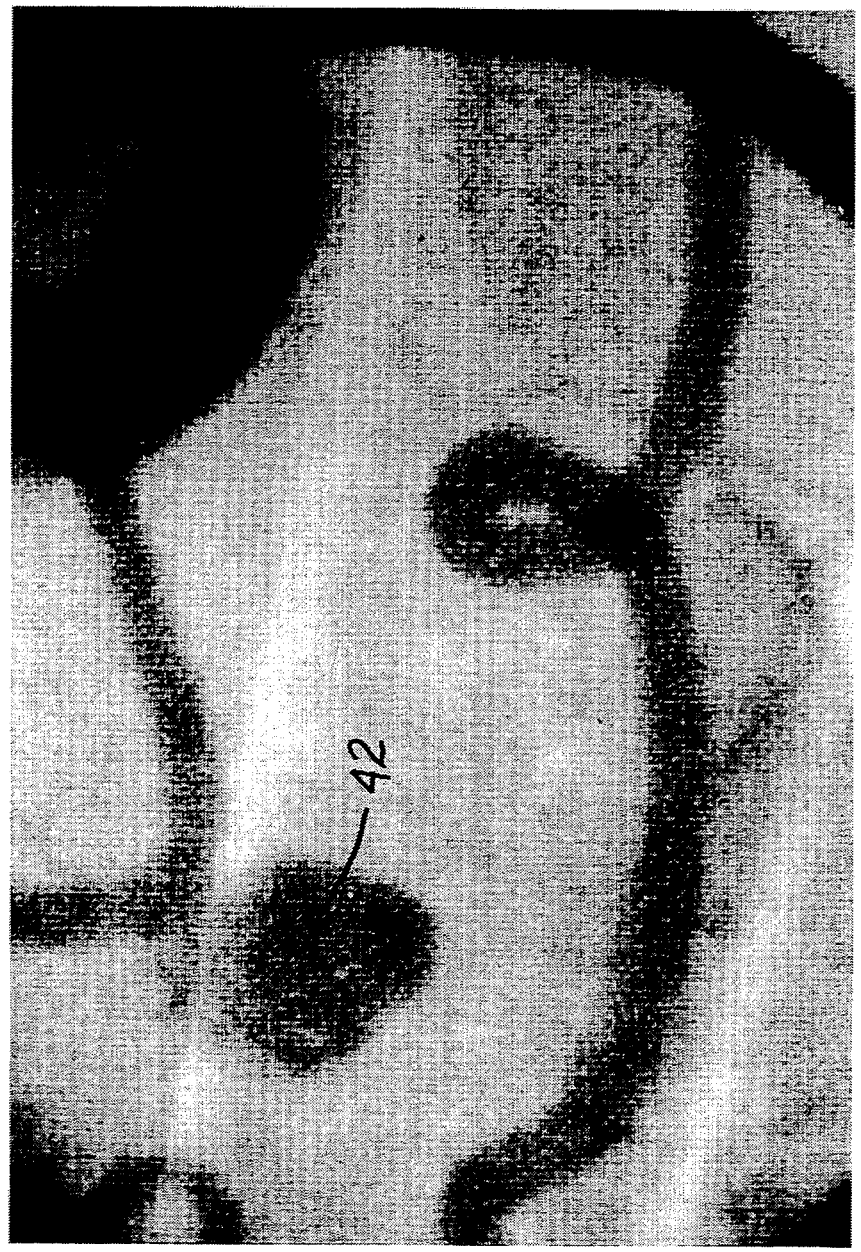

FIG. 3b illustrates a magnified image obtained upon zoom operation of the image shown in FIG. 3a as coupled through lens 32 and CCD camera 30 to video processor 22 and displayed on monitor 34. Either or both images are provided in hard copy record to laser printer 36. Brain aneurysm 42 measures 4 millimeters in actual size and is magnified 20 times to be displayed as an 80 millimeter image at monitor 34 using full zoom, 16 frame integration in a 4.5-inch mode of the image intensifier. The display magnification of 20 is monitor size-dependent, and due to the large display magnification, the pattern of structured noise arising from the pixels of the CCD camera 30 are visible in the images at maximum zoom condition. It is expected that different magnifications and image noise patterns will be realized through the use of different CCD-type cameras and monitors according to user choice.

Figure 2A:
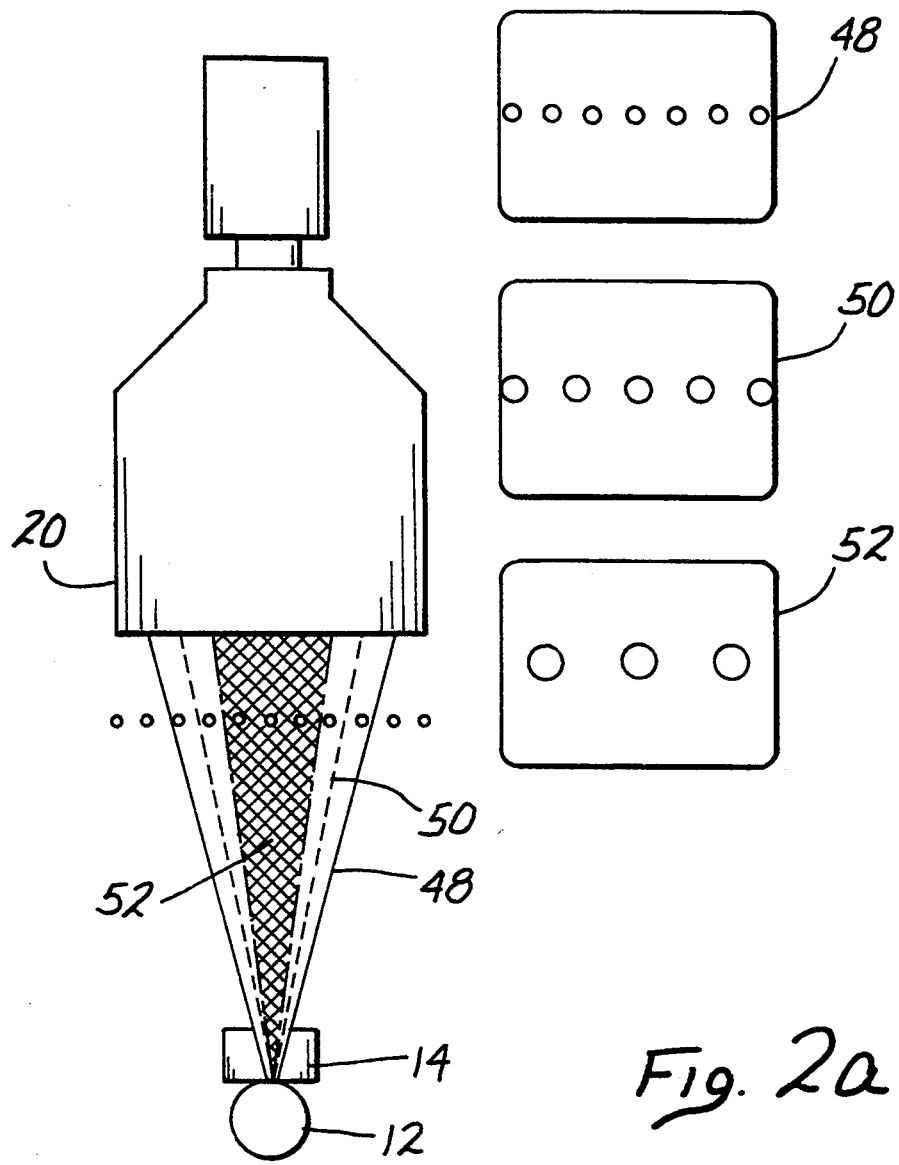
FIGS. 2a and b are diagrammatic depictions illustrating the coordination between optical zoom magnification and x-ray collimation of the beam.
Figure 2B:
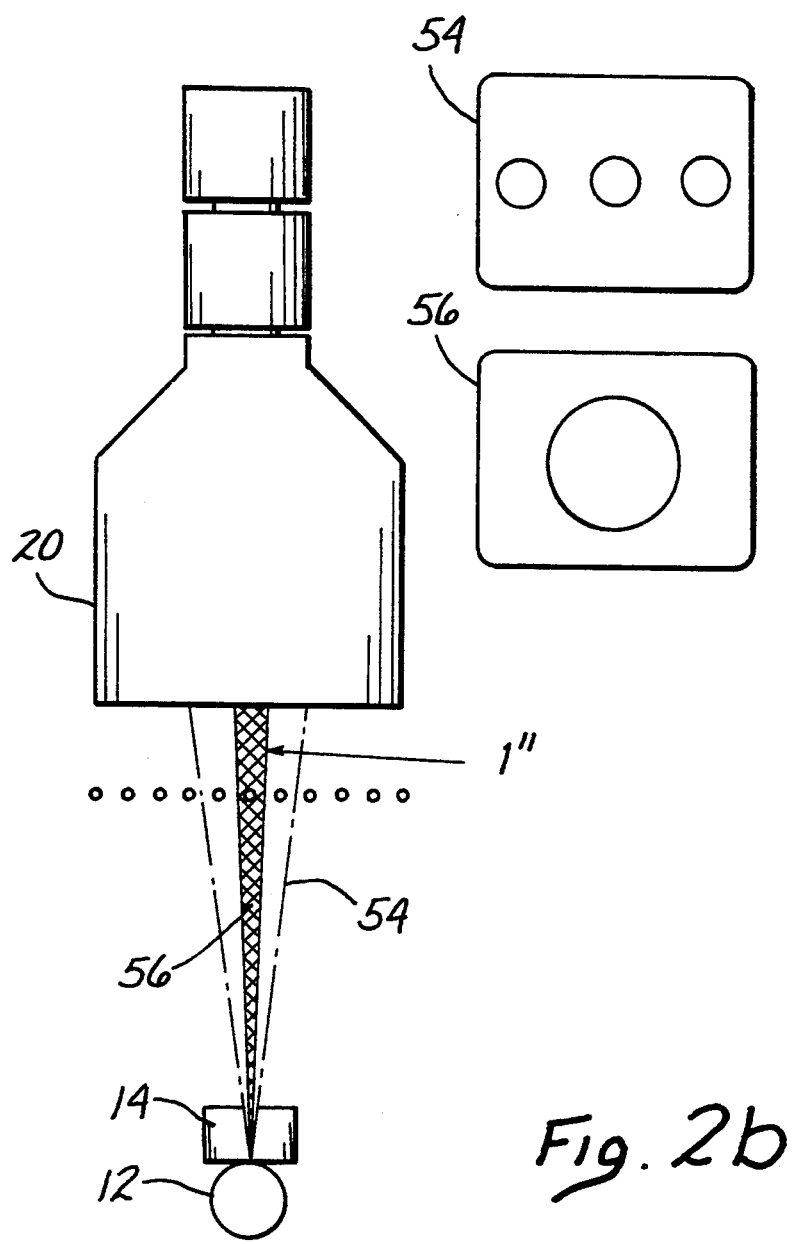

FIGS. 2a and b illustrate the result of coupling collimator 14 with zoom lens 32 in the collimation of the x-ray beam. FIG. 2a illustrates X-ray source 12 collimated by collimator 14 onto the imaging face of image intensifier 20 according to the conventional 9-inch, 6-inch, and 4.5-inch collimation modes which provide the images 48, 50 and 52 respectively as shown in FIG. 2a when the conventional camera is used to provide a macroscopic view of the region of interest. FIG. 2b illustrates a more narrow coning of the x-ray beam, which collimation is used and coordinated with the operation of the zoom lens when the zoom lens and CCD camera of the improvement is used to provide an image of the field of interest. Collimator circuitry 38 has been modified to provide an accurate collimation as the maximum field of view an image 54 and a minimum field of view corresponding to an image 56 shown in FIG. 2b. A specifically designed circuit provides a feedback signal from the motorized zoom lens control of the Canon lens to the x-ray collimator. This feedback signal is then used to drive the collimator.

Figure 4A:
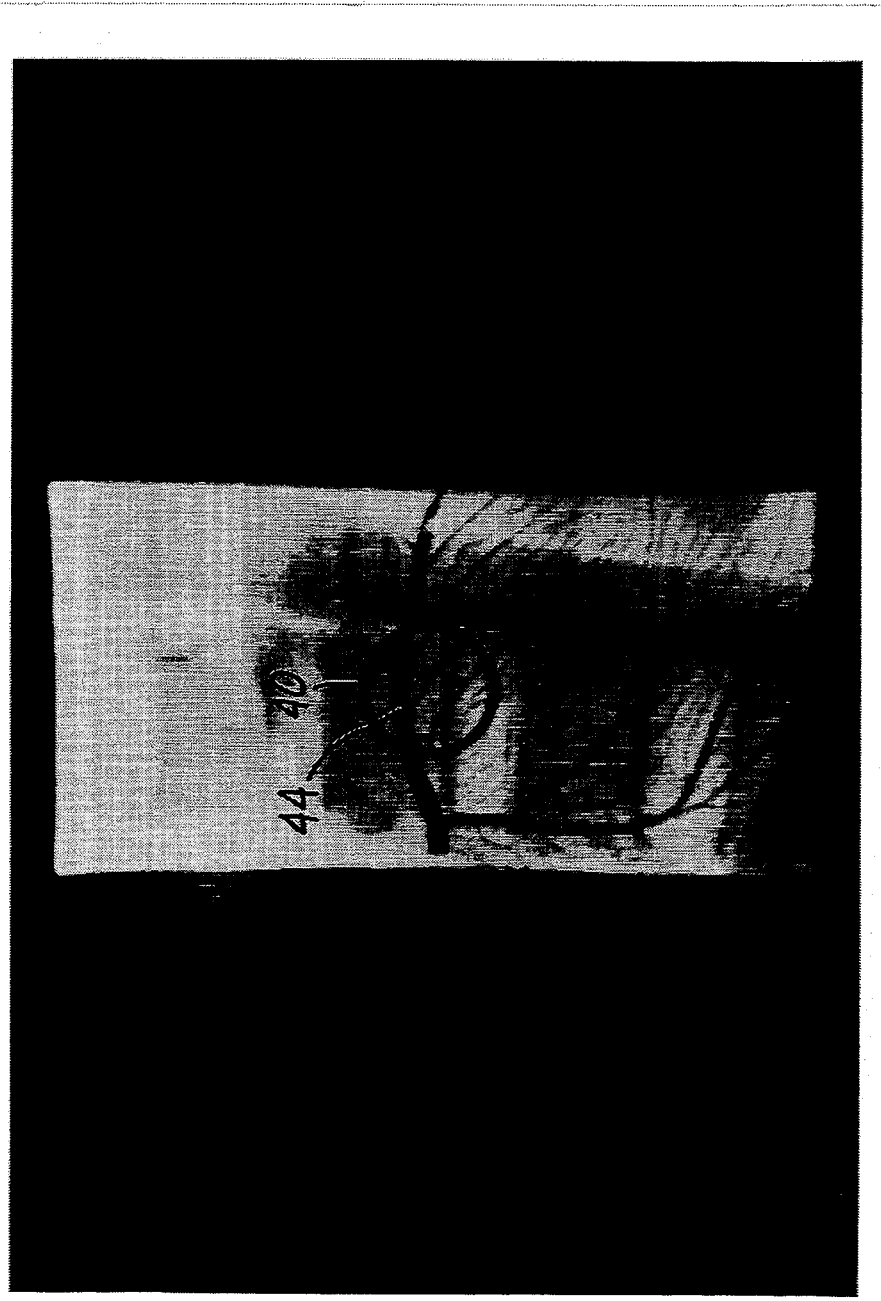
FIGS. 4a and b are fluoroscopic images of a stenotic regions in a heart phantom shown in a macroscopic and magnified view respectively as provided by a fluoroscopic system improved according to the invention.
Figure 4B:
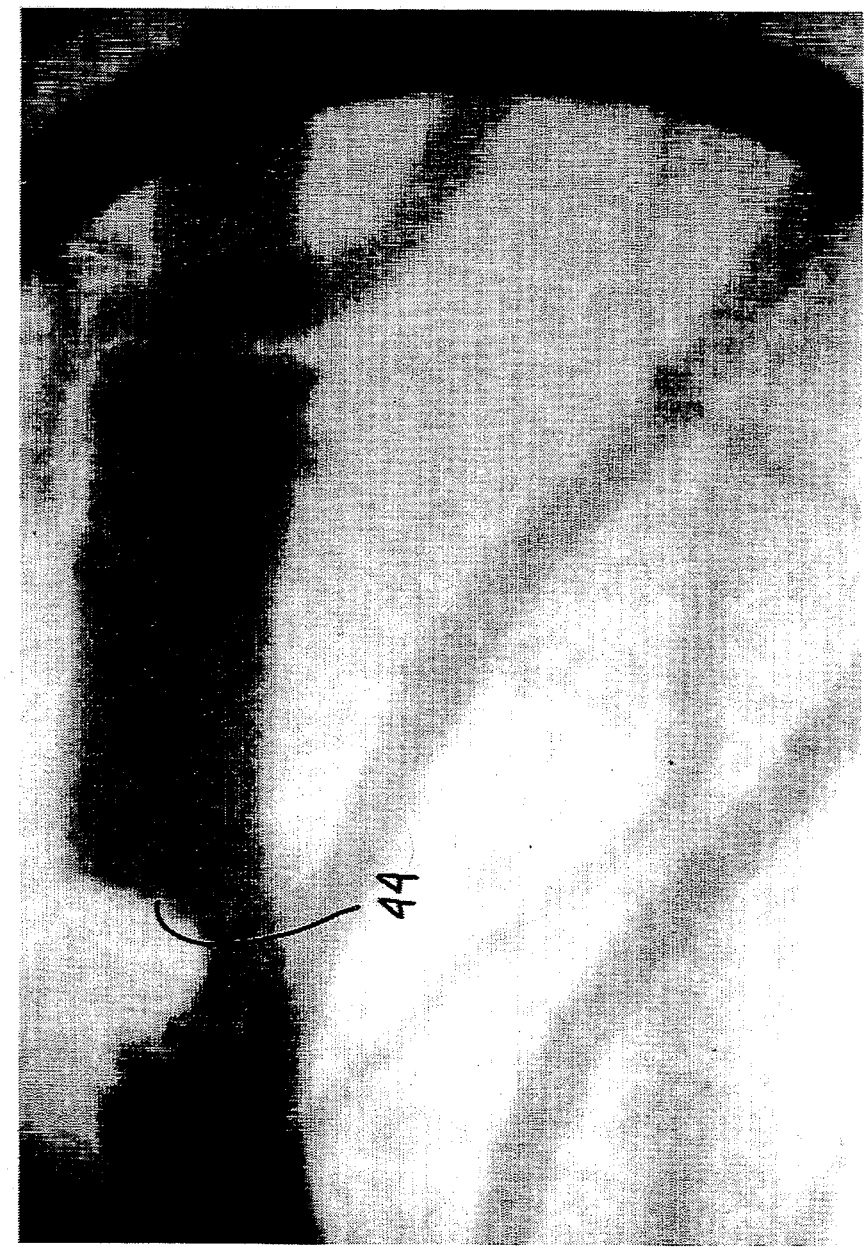

FIGS. 4a and b illustrate the output of the system when used on a modified chest phantom, having a coronary artery tree formed of iodinated plastic. Stenotic regions are incorporated at various locations in the vascular pattern as shown in FIG. 4a including within the region of interest 40 a stenotic region 44. FIG. 4a shows a 9-inch view of the coronary artery pattern superimposed upon a chest phantom, while FIG. 4b illustrates region of interest 40 at maximum magnification. A 1.5 millimeter coronary arterial stenoses appears on the monitor 34 as a 25 millimeter lesion 44 under full magnification using 16 frame integration and 4.5-inch mode on image intensifier.

Figure 5A:
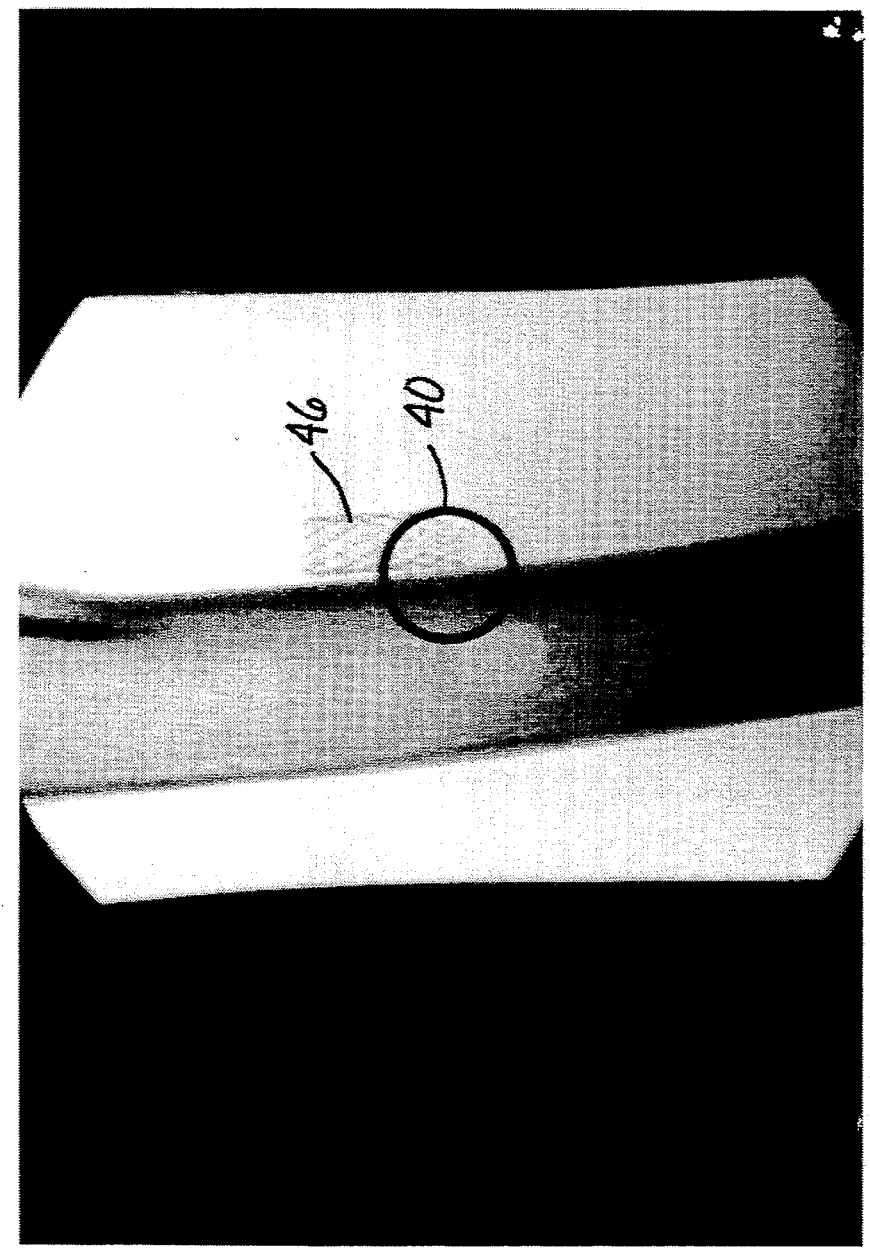
FIGS. 5a and b are fluoroscopic images of an arterial stent in a leg in a phantom shown in a macroscopic and magnified view respectively as provided by a fluoroscopic system improved according to the invention.
Figure 5B:
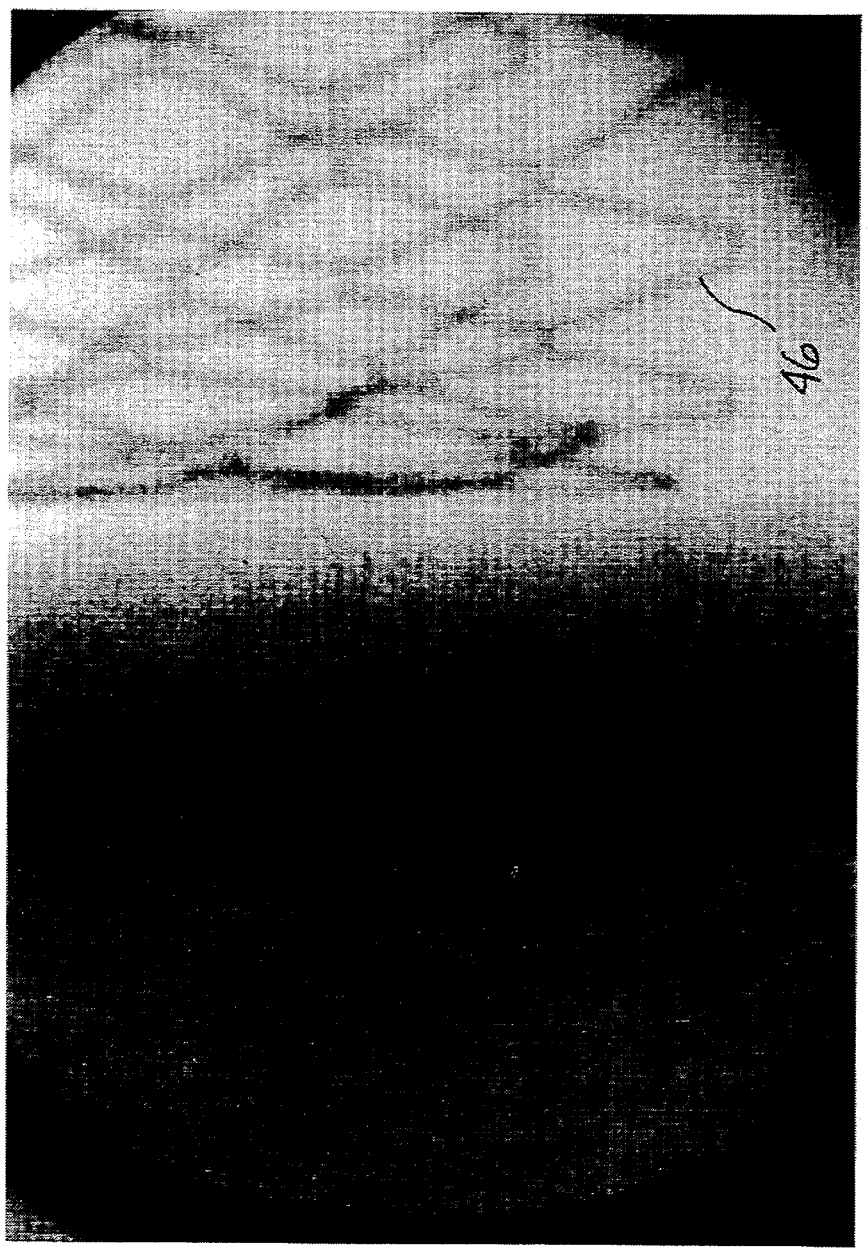

Placement of a stent 46 in the superficial femoral artery of a leg phantom is illustrated in FIGS. 5a and b. Stent 46 is a 316L Palmaz (Johnson & Johnson Interventional Systems of Warren, N.J.) stent. FIG. 5a illustrates a 9-inch view of a leg section of a phantom showing stent 46 as would be seen in monitor 26. FIG. 5b is a magnified image as shown through camera 30 on monitor 34 in which the 150 micron struts of the Palmaz stent 46 are clearly imaged.

In the present invention, the utilization of a noise reduction/image storage device provides the attending physician with a parallel full field display which is rapidly updated by instantaneously switching back to camera 24-by means of an electromechanically moveable minor within beam splitter 28. This mode of operation overcomes the loss of orientation due to patient motion during magnification fluoroscopy.

The use of high X-ray exposure rates is avoided through the use of electronic noise reduction. The microfocal spot of the system permits application of the air gap scatter clean up method without loss of spatial resolution caused by geometric magnification. Due to the small cross section of the x-ray beam, the scatter grid can be removed from the system during zoom operation thereby resulting in an increased input exposure rate to the image detector.

Under maximum zoom conditions, the narrow collimation of the radiation beam passing through the patient to project only a 1-inch diameter image onto the input window of imaging intensifier 20 increases the fluoroscopic contrast resolution due to scatter reduction.

A further advantage of the narrow field of view is that only the most linear part of the curved face of image intensifier 20 input is utilized, thereby resulting in an image, which is virtually free of pin-cushion distortion and of luminance inhomogenities, which are common to large field of view within image intensifiers.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the germ of the invention.

We claim:

1. An improvement in a system for X-ray fluoroscopic video imaging having an image intensifier for generating a dynamic radiographic image of an X-ray pattern and a monitor system for displaying said dynamic radiographic image, said improvement comprising:

an X-ray source;

an X-ray collimator coupled to said X-ray source, said X-ray collimator having variable collimation; and a variable magnifying lens for optically magnifying a selected smallest area of interest of said dynamic radiographic image of said image intensifier;

a sensitive video camera optically coupled to said magnifying lens for generating a video signal to be sent to said monitor system, wherein said monitor system displays an image of said X-ray pattern provided by said sensitive video camera;

means for selectively varying collimation of X-rays by said X-ray collimator in coordination With the degree of magnification provided by said magnifying lens to maintain total X-ray dosage below a predetermined maximum., whereby magnified images of said X-ray pattern are provided in video signal format with submillimeter resolution and at a display format on said monitor system large enough to present an enlarged dynamic, real-time presentation to a user while allowing said user to operate within a sterile field while a minimum x-ray exposure is always provided for said selected smallest area of interest.

2. The improvement of claim 1 wherein said magnifying lens is a selectively variable color television zoom lens.

3. The improvement of claim 1 wherein said zoom lens has a center with maximum resolution and wherein said video camera is always positioned at said center to utilize maximum resolution of said lens.

4. The improvement of claim 1 wherein said magnifying lens is continuously variable.

5. The improvement of claim 1 further comprising:

a video camera for generating a video signal to be sent to said monitor system, wherein said monitor system displays an image of said X-ray pattern provided by said video camera as part of a low resolution video channel; and an optical beam splitter optically coupled to said image intensifier and having one optical output coupled to said magnifying lens and a second optical output optically coupled to said camera in said low resolution video channel.

6. The improvement of claim 5 wherein said optical beam splitter selectively transmits said dynamic radiographic image from said image intensifier either to said magnifying lens or to said camera in said low resolution video channel upon user command.

7. A fluoroscopic system comprising:
an X-ray source for producing X-rays;
a variable X-ray collimator coupled to said X-ray source;
a scanning table for positioning a patient above said X-ray source and collimator in a selected position subject to operator control;
an image intensifier for receiving an X-ray pattern received from said patient and for generating a dynamic radiographic image thereof;
an optical beam splitter optically coupled to said image intensifier for selectively directing said dynamic radiographic image in a selected one of a first and second direction;
a television camera optically coupled to said beam splitter for receiving said dynamic radiographic image along said first direction to comprise a low resolution video channel;
a digital video processor coupled to said television camera for processing video information received from said television camera to selectively produce a digitally processed display of said dynamic radiographic image;
a variable zoom lens optically coupled to said optical beam splitter for receiving and variably magnifying said dynamic radiographic image from said image intensifier when said dynamic radiographic image is transmitted by said optical beam splitter along said second direction; and
a sensitive television camera for generating a video signal coupled to said variable zoom lens to comprise a high resolution video channel, said high resolution television channel being coupled to said digital video processor,
wherein said digital video processor for processing video information received from said high resolution video channel simultaneously displays a second digitally processed video image from said low resolution video channel, said second image being stored in said digital video processor; and
wherein said variable collimator being selectively controlled to collimate said X-rays from said X-ray source in coordination with the degree of magnification provided by said variable zoom lens, magnification of said variable zoom lens being simultaneously controlled with said variable collimator so that a smallest area of interest is exposed to said X-rays while said variable zoom lens provides maximum magnification for said smallest area of interest to maintain total x-ray dosage below a predetermined maximum,
whereby magnified images of said X-ray pattern are provided in video signal format with submillimeter resolution and at a display format on said monitor system large enough to present an enlarged dynamic, real-time presentation to a user while allowing said user to operate within a sterile field.

8. The fluoroscopic system of claim 7 wherein said digital video processor processes video information from said high resolution television channel and from said low resolution television channel to integrate multiple frames of video information to reduce noise and to display digitally enhanced images of said dynamic radiographic image reduced by said noise integration.

9. The fluoroscopic system of claim 7 further comprising recording means for producing a permanent record of said displays generated by said digital video processor.

10. The fluoroscopic system of claim 7 wherein said image intensifier produces said dynamic light image at a predetermined wavelength, and wherein said variable zoom lens has a center with maximum optical resolution and is arranged and configured for maximal transmission at said wavelength and maximum resolution of said smallest area of interest by always focussing said smallest area of interest at said center of said zoom lens.

11. A method for performing submillimeter, high resolution fluoroscopy on a real-time basis comprising the steps of:
positioning a patient within a fluoroscopic X-ray system to bring an object of interest within said within said patient into a predetermined field of view defined as the smallest region of interest by observing fluoroscopic images of said object of interest through a low resolution video channel and a real-time television display system;
redirecting fluoroscopic examination of said region of interest to a high resolution channel focused on said smallest region of interest through said fluoroscopic system by means of a variable zoom lens;
displaying on real-time basis a video image produced by said high resolution video channel;
simultaneously adjusting the magnification of said zoom lens until a desired degree of magnification is achieved; and
simultaneously collimating an X-ray beam to which said patient is exposed to develop said fluoroscopic image of said object of interest in coordination with said step of simultaneously controlling magnification of said zoom lens, said step of collimating said beam increasing collimation of said X-ray beam as magnification of said dynamic radiographic image increases through control of said variable zoom lens to maintain X-ray dosages at or below a predetermined minimum,
whereby orientation of said object of interest is established through said low resolution channel and immediately switched for detailed examination through said zoom lens and high resolution channels.

12. The method of claim 11 where said of step of redirecting comprises the step of actuating a beam splitter to direct a dynamic radiographic image of an X-ray pattern of said object of interest selectively to said low or high resolution channel as determined by operator control.

13. The method of claim 11 further comprising the step of integrating multiple frames of video information derived from said low resolution and high resolution channels to provide during said step of displaying said video image a reduced noise video image.

14. The method of claim 11 further comprising the step of generating a dynamic radiographic image of said X-ray pattern within a narrow optical bandwidth, said zoom lens and high resolution video channel optimized to operate within the narrow bandwidth of light to increase the optical sensitivity.

15. The method of claim 11 comprising the steps of repeating said step of positioning said patient when patient movement causes loss of orientation of said object of interest, said patient being selectively positioned by performing said step of redirecting said dynamic radiographic image of said X-ray pattern to said low resolution channel to reorient said object of interest within said region of interest within said system, and thereafter repeating said step of redirecting said dynamic, radiographic image to said high resolution television channel once reorientation of said object of interest within said region of interest is established.

* * * * *